US006183451B1

United States Patent
Mehl, Sr. et al.

(10) Patent No.: US 6,183,451 B1
(45) Date of Patent: Feb. 6, 2001

(54) METHOD OF DELIVERY OF SKIN TREATMENT AGENTS USING FREEZE-DRIED LIPOSOMES

(76) Inventors: Thomas L. Mehl, Sr., P.O. Box 1019, Newberry, FL (US) 32669; Nardo Zaias, 5189 Alton Rd., Miami Beach, FL (US) 33140

( * ) Notice: Under 35 U.S.C. 154(b), the term of this patent shall be extended for 0 days.

(21) Appl. No.: 09/204,902

(22) Filed: Dec. 3, 1998

Related U.S. Application Data

(60) Division of application No. 08/634,183, filed on Apr. 18, 1996, now Pat. No. 5,885,260, which is a continuation-in-part of application No. 08/423,939, filed on Apr. 19, 1995, now abandoned, which is a continuation of application No. 08/066,261, filed on May 25, 1993, now abandoned, which is a continuation-in-part of application No. 07/929,750, filed on Aug. 17, 1992, now abandoned, which is a continuation-in-part of application No. 07/707,828, filed on May 30, 1991, now abandoned.

(51) Int. Cl.[7] .................................................. A61M 35/00
(52) U.S. Cl. ............................................................ 604/290
(58) Field of Search ..................... 604/289, 290, 604/304, 305, 308; 424/365, 450, 94.5

(56) References Cited

U.S. PATENT DOCUMENTS

| | | |
|---|---|---|
| 2,736,317 | 2/1956 | Alexander . |
| 4,311,712 | 1/1982 | Evans et al. ........................ 424/365 |
| 4,370,349 * | 1/1983 | Evans et al. ........................ 424/365 |
| 4,830,858 | 5/1989 | Payne et al. ........................ 424/450 |
| 4,880,635 | 11/1989 | Janoff et al. ........................ 424/450 |
| 5,034,228 | 7/1991 | Meybeck et al. ................... 424/401 |
| 5,106,624 | 4/1992 | Bertini ................................ 424/401 |
| 5,128,139 | 7/1992 | Brown ................................ 424/450 |
| 5,190,762 | 3/1993 | Yarosh ............................... 424/450 |
| 5,439,672 | 8/1995 | Zabotto .............................. 424/59 |
| 5,476,852 | 12/1995 | Cauwenbergh ..................... 514/252 |
| 5,489,426 | 2/1996 | Zabotto .............................. 424/59 |
| 5,607,409 | 3/1997 | John . |

FOREIGN PATENT DOCUMENTS

| | | |
|---|---|---|
| 0160266 | 4/1985 | (EP) . |
| WO 87/01938 * | 4/1987 | (WO) . |
| WO87/01938 | 5/1987 | (WO) . |
| WO94/28876 | 12/1994 | (WO) . |

* cited by examiner

*Primary Examiner*—John G. Weiss
*Assistant Examiner*—David J. Cho
(74) *Attorney, Agent, or Firm*—Sven W. Hanson

(57) ABSTRACT

A method and article for delivery of skin care agents. Freeze-dried liposomes are used to encapsulate agents for delivery to specific cells in the skin. The applicable agents include perfumes, moisturizers, vitamins and therapeutic compounds as well as others. The agents are encapsulated in liposomes specifically selected to carry the agents to the target cells thereby increasing effectiveness and efficiency and minimizing systemic absorption. The liposomes are at least partially freeze-dried to improve shelf-life and improve delivery to the skin. After freeze-drying, the liposomes are deposited on or in a fabric-like pad. The liposomes are rehydrated either immediately prior to application to the skin or on the skin using natural moisture or a hydrating solution. An applicator is also provided to secure and hold the impregnated pad during use. The applicator may provide steam or vapor to rehydrate the liposomes during application.

12 Claims, 3 Drawing Sheets

METHOD OF DELIVERY OF SKIN TREATMENT AGENTS USING FREEZE-DRIED LIPOSOMES

RELATED APPLICATIONS

This application is a divisional application of application Ser. No. 08/634,183 (Issued Mar. 23, 1999 as U.S. Pat. No. 5,885,260 filed Apr. 18, 1996 is a continuation-in-part of application Ser. No. 08/423,939, filed Apr. 19, 1995 (abandoned), which is a continuation of application 08/066,261, filed May 25, 1993 (abandoned), which is a continuation-in-part of application 07/929,750, filed Aug. 17, 1992 (abandoned), which is a continuation-in-part of application 07/707,828, filed May 30, 1991 (abandoned), and each of which is incorporated herein by reference.

BACKGROUND OF THE INVENTION

The present invention pertains to the delivery of beneficial agents to skin cells using liposomes in a delivery system. Particularly, the invention involves a system in which skin care compounds are encapsulated in a freeze dried liposome.

The ability of liposomes to encapsulate, carry, and deliver agents to specified cells within the human body is well known. However, little has been done to integrate liposome encapsulated agents into practical skin care procedures and methods. What is needed is a system which combines the beneficial properties of liposomes in practical skin care processes and products.

SUMMARY OF THE INVENTION

It is an objective of the present invention to provide a system for liposome delivery of skin care products which maximized the benefits of liposome technology by increasing shelf life and flexibility of application.

It is another objective of the present invention to provide a method of encapsulating effective agents to be stored and activated at the time of use.

It is another objective of the present invention to provide skin care products in a form which are most effectively carried to the target tissue.

It is also an objective of the present invention to provide a system for application of liposome encapsulated therapeutic agents for enhanced treatment of the skin using a hand held applicator for ease of use.

It is a further objective of the invention to provide an article and method for application of therapeutic agents in freeze-dried liposomes using steam and vapor as a method of rehydration.

It yet another objective of the invention to provide a hand-held applicator to facilitate effective application of agents encapsulated in freeze-dried liposomes.

By encapsulating skin care agents in freeze-dried liposomes the present invention provides a practical method of utilizing the advantages of the liposome structure in effective delivery of skin care products to the skin tissue. This invention takes advantage of the ability of liposomes to deliver agents to specific cells and tissues in the human body. By introducing freeze-drying of liposome encapsulated skin care agents the full benefits of liposome delivery are utilized.

Liposomes especially designed for application to the skin are selected in order to deliver the effective agents to the specific tissue sites requiring treatment. This increases the effectiveness and efficiency of the applied agent. The agents considered include pharmaceutically active compounds including ketoconazole; antioxidants; botanical extracts; alpha hydroxy acids; fruit derived extracts and acids; fragrances; minerals; moisturizers; urea; proteinases such as papain; and vitamins. The liposome encapsulated agents are freeze-dried to improve both shelf-life, increase stability of the liposomes and the encapsulated agents, and add flexibility of application.

In a freeze-dried form, the agents may be effectively applied to the skin in a variety of manners including simple application to the skin by the users fingers. A hand held steam device is introduced to enable more effective application of the freeze-dried liposomes.. This device is designed to provide a supply of steam for reconstitution of the liposomes and agent at the moment of contact with the skin. A fabric pad is also provided on which is deposited a single or multiple freeze-dried liposome encapsulated agents can be secured to the steam device to ease application. Multiple fabric pads may be prepared with a variety of freeze-dried liposomes prior to the time of application and stored allowing for selection at the time of use.

DESCRIPTION OF THE PREFERRED EMBODIMENTS

Figure 1:
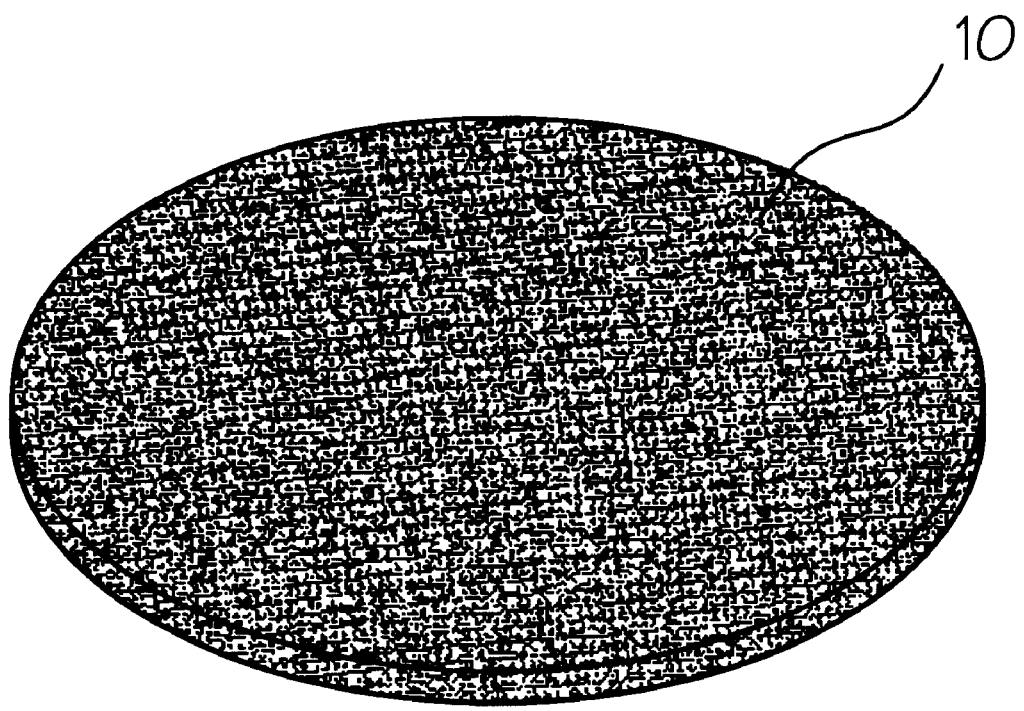
FIG. 1 is a perspective view of a fabric-like pad.

The delivery system of the present invention improves the particular characteristics of liposomes to store and carry agents to the human epidermis in an efficient and effective manner to improve the skin condition. By freeze-drying the liposomes, the problems of stability and shelf-life of the liposomes and agents are overcome and a practical form for application is produced. This is furthered by use of a fabric pad for carrying and applying the freeze-dried liposomes. The agents considered are those directed to skin in either a healthy or pathological conditions. Generally, the delivery system includes the processes of selection and preparation of specific liposomes for delivery to the epidermis, encapsulation of the specific effective agents, freeze drying, followed by topical application which may include transformative steps.

Liposomes provide a non-toxic means for encapsulation of agents and can be further modified to bind to specific sub-populations of cells. Specifically, the liposome membranes according to the present invention can be made to bind to specific cells or sites within the epidermis. An advantage of this characteristic is the ability to reduce migration of particular agents into the dermis and blood stream. This can allow for local application of agents which otherwise penetrate the skin barrier too readily and cause systemic problems. In addition, dilution of the effective agents is reduced minimizing the required application. However, where delivery of agents to the dermal region is desired, the present invention is also applicable. In such case, liposome selection is directed to binding to cells below the epidermis/dermal boundary.

Liposomes are microscopic and larger membrane-enclosed vesicles or sacs made artificially in the laboratory by a variety of methods. They are generally spherical but may be form in other shapes as well. The primary requirements according to the present invention are that the liposomes should not be toxic to the living cells and that they should preferentially bind to, or otherwise reside among, the cells of the epidermal layer of the skin. The liposomes according to the present invention may be of various size and may comprise either one or several membrane layers separating the internal and external compartments. An important element in liposome structures is that the liposome be resistant to destruction as it travels from the surface of the skin down to the target region. Liposome structures according to the present invention include small unilamellar vesicles (less than 250 angstroms in diameter), large unilamellar vesicles and multilamellar vesicles.

The liposomes according to the present invention may be made from natural and synthetic phospholipids, glycolipids and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activities. Liposomes may also be formed of mixtures of the above compounds.

Encapsulation of the desired agent in liposomes may be effected by combining a phospholipid component with an aqueous component containing the selected agent under conditions which will result in vesicle formation. The phospholipid concentration must be sufficient to form lamellar structures, and the aqueous component must be compatible with the agent to be encapsulated. Methods for combining the phospholipid and the aqueous components so that vesicles will form include: drying the phospholipids onto glass and then dispersing them in the aqueous components; injecting phospholipids dissolved in a vaporizing or non-vaporizing organic solvent into the aqueous component which has previously been heated; and dissolving phospholipids in the aqueous base with detergents and then removing the detergent by dialysis. The liposomes can be produced from the foregoing mixtures either by sonication or by dispersing the mixture through either small bore tubing or through the small orifice of a French Press. The methods for producing the liposomes as set forth in U.S. Pat. 5,077,211 to Yarosh are incorporated herein by reference.

It is within the scope of the present invention to use other methods for encapsulating agents within a liposome. A specific example of producing the liposomes would include the following process. A lipid mixture as set forth above is dissolved in an organic solvent and dried to a thin film in a glass vessel. The selected agent is purified and added to the vessel at high concentrations in an aqueous buffer to rehydrate the lipid. The mixture is then agitated by vortexing and sonicated to form liposomes. The liposome spheres containing the encapsulated agent are then separated from the unincorporated agent by centrifugation or gel filtration.

Administration to humans requires that the liposomes be pyrogen-free and sterile. To eliminate pyrogens, pyrogen-free raw materials, including all chemicals as well as the agents and water are used to form the liposomes. Sterilization can be performed by filtration of the liposomes through a 0.2 micron filter. A general discussion of liposomes and liposome technology can be found in a three volume work entitled Liposome Technology edited by G. Gregoriadis, 1993, published by CRC Press, Boca Raton, Fla. The pertinent portions of these references are incorporated herein by reference.

A broad variety of agents may be liposome encapsulated for application to the skin. A few of the potential agents include one or more of the following types or compounds: pharmaceutically active compounds including antimicrobials; antioxidants; botanical extracts; alpha hydroxy acids; fruit and vegetable derived extracts and acids; fragrances; minerals; moisturizers; urea, proteinases such as papain and ananase; and vitamins or combinations thereof The present invention includes the use of both water-soluble and hydrophobic (oil-soluble) compounds in the same liposome. U.S. Pat. No. 5,128,139 to Brown, etal., and U.S. Pat. No. 5,439,672 to Zabotto, etal., are incorporated herein as examples of encapsulation of cosmetic agents in liposomes.

Following encapsulation, the liposomes are freeze-dried to remove their water content. Freeze-drying greatly expands both the utility of liposomes for skin care purposes and the range of application methods. Liposomes in aqueous dispersions generally have limited physical stability and shelf life. Individual liposome particles in dispersions tend to associate and coalesce, forming larger liposome particles. Also, the agents may diffuse into the dispersing solution. In addition, the structural or agent components of a liposome in a dispersion may be lost due bacteriological, enzymatic, and/or chemical reaction degradative processes facilitated by the dispersing medium. Freeze-drying liposomes considerably reduces these problems by reducing the time the liposomes are in a liquid phase, and provides for storage with far less opportunities for loss of integrity of either the structural component or the agent materials. Freeze-drying of liposomes can be accomplished by various means known to those skilled in the art. See "Preservation of Liposomes by Freeze-Drying", Vol. 1, p. 229, in LIPOSOME TECHNOLOGY, LIPOSOME PREPARATION AND RELATED TECHNIQUES, ed. by Gregory Gregoriadis, CRC Press, Boca Raton, 1993.

The addition of certain disaccharide sugars to the liposome-forming mixtures has been shown to improve stability upon rehydration of the freeze-dried liposomes. This effect is discussed in the above reference. Although other sugars, such as sucrose, may be suitable for certain liposome compositions, trehalose has been found to be the preferred additive.

Once the desired topical agent has been encapsulated in the appropriate liposome and the liposomes freeze-dried, this material may be prepared in a variety of forms for application to the skin. The liposomes may be packaged alone for use as a single constituent of a skin treatment material. However, the freeze-dried liposomes may also be combined with secondary ingredients.

In the freeze-dried state, the liposomes may be applied directly to the skin. The natural moisture found on and in the skin will rehydrate the liposomes effectively activating them to carry the encapsulated agent into the skin. Rehydration can also be assisted by applying additional moisture to the skin prior to, after, or with the application of the freeze-dried liposomes. Alternatively, water or water vapor may be used to rehydrate the liposomes immediately before use.

Application of the liposomes and addition of moisture may be accomplished in a variety of ways. The simplest may be by rubbing the liposomes directly onto the skin using the fingers. In a preferred embodiment, prepared liposomes are deposited within or onto a substantially fibrous or polymeric pad 10 (see FIG. 1) which is then put into contact with the skin to apply the liposomes. It is preferred that an binding agent 15 be applied to the pad 10 prior to depositing liposomes to assist in capture and adherence. The pad 10 may be made of natural fibers, filament fiber material, synthetic polymers, and any other materials having fabric-like properties. Various pad materials are known and used in the skin care industry for skin care applications. The pad 10 may also be formed of sponge-like materials in which a greater quantity of liposomes or a secondary agent may be deposited. Preferably, liposomes are deposited on the outer surface of the pad 10 such that contact with the skin is maximized and the amount of liposomes used is minimized. The liposomes may be deposited onto the pad 10 at the time of use or, preferably, the pad 10 is preimpregnated and then stored in a vapor-proof container or other packaging designed to reduce moisture contamination such as with a desiccant. This second alternative makes most use of the benefits of the liposomes in a commercial setting. That is, the liposomes themselves need not be handled, thereby preventing accidental hydration.

Use of such a pad 10 simplifies the hydration process. A pad 10 containing liposomes may be dipped into a hydrating solution, allowing for full reconstitution of the liposomes immediately before application to the skin. The hydrating solution may also contain secondary ingredients such as moisturizers. However, such secondary ingredients are limited to those which will not unduly disrupt the specific liposome structure.

In a typical application, freeze-dried liposomes are formed using the above process. The encapsulated agent being the antifungal compound ketoconazole. The freeze-dried liposomes are deposited on one side of a fibrous pad 10. The pad 10 then is sealed in a nitrogen flushed foil package. The protective wrapper is opened just prior to use, and the pad 10 rubbed onto the skin areas of concern which have been premoistened. Disruption of a portion of the liposomes occurs at the skin surface as a consequence of the mechanics of application and chemicals residing on the skin. As a result, ketoconazole is released to effect its purpose as a antifungal. A second portion of the liposomes survives to penetrate the epidermis to deliver ketoconazole to the sebaceous glands. Systemic absorption is minimized by liposome encapsulation.

Figure 2:
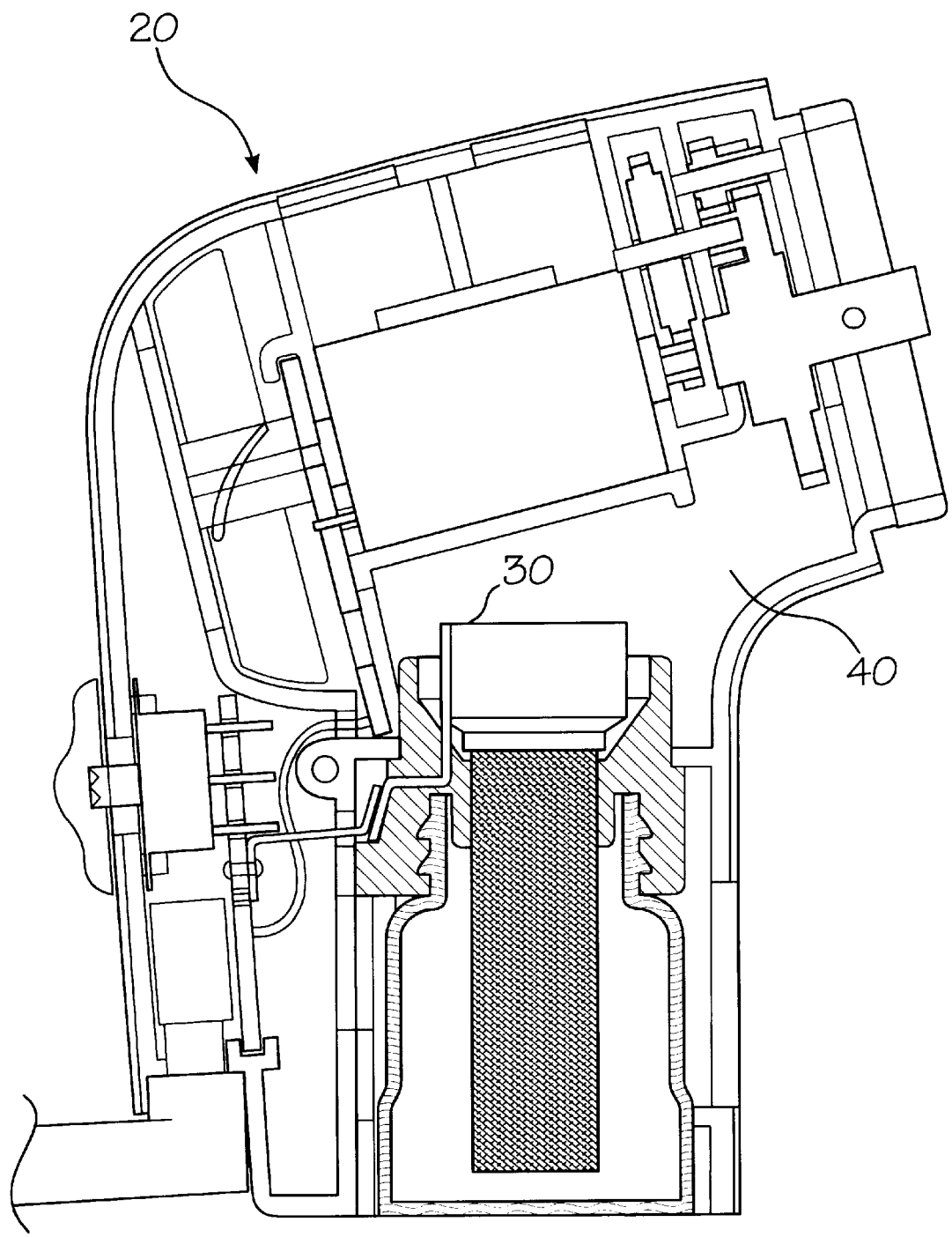
FIG. 2 is a cross-sectional view of a hand-held steaming device showing details of an internal steam generator.

Advantages can be gained by incorporating the above pad 10 into a hand held applicator such as the steam device 20 shown in FIG. 2. An obvious advantage is the ease of grasping and applying a fabric pad 10 when an applicator is provided as a "handle". Additionally, the applicator of the present invention allows for: minimizing contact with the fingers; exposing the area of the pad 10 containing the liposome directly and completely to the targeted skin area; providing steam or vapor for rehydration; and providing a means for applying uniform or concentrated pressure.

Figure 3:
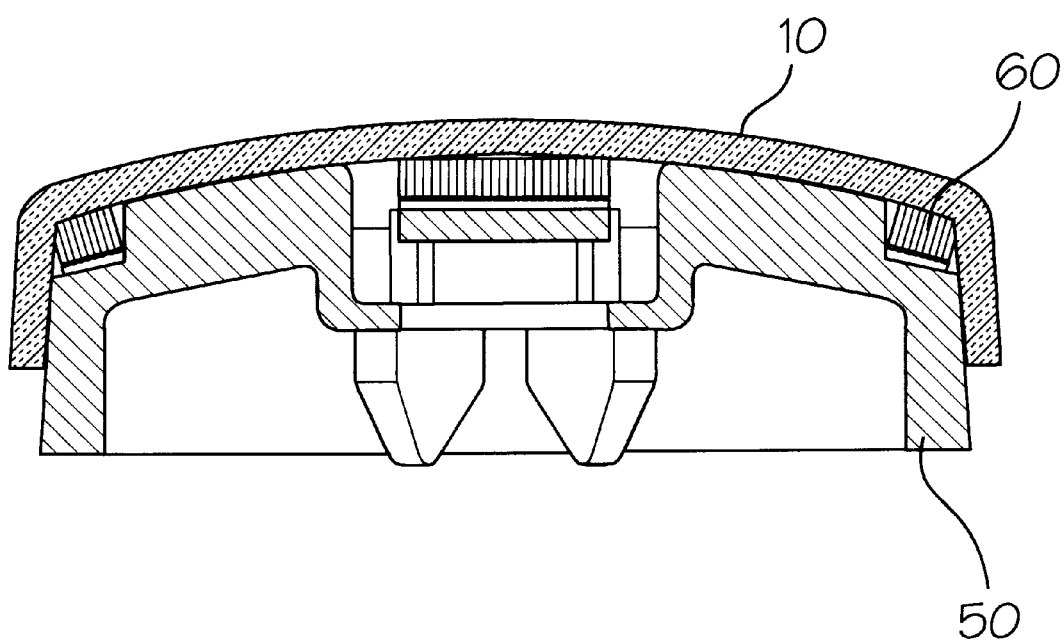
FIG. 3 is a cross-sectional view of an adapter for securing a pad to a hand-held steaming device.

Another advantage of an applicator such as the steam device 20 is that of providing water vapor or steam as a liposome rehydrating means. The steam device 20 shown in FIG. 2 incorporates an internal steam generator 30 which produces steam and vapor that can be directed through an internal passage 40 such as to flow through an attached pad. In practice, the pad 10 containing freeze-dried liposomes may be secured to the steam device 20 via an adapter 50 shown in FIG. 3 by a securing means 60 such as Velcro®. In this position, rehydration may be effected by manual addition of an separate aqueous solution. Preferably, however, the liposomes are directed onto the skin simultaneous with steam or vapor being directed through the pad 10 and onto the skin. In this manner, the liposomes are hydrated at the moment of application. Depending on the quantity and temperature, application of steam will cause some degree of disruption of the liposome structure thereby releasing the effective agent. This may be controlled by regulating the steam energy used. In specific applications this method may be used to cause early release where the agent is desired to act at the skin surface as well as through liposome delivery. The above described and depicted device is but one example devices which may be used for application of freeze-dried liposomes. It will be obvious to one skilled in the art to use similar devices in the current invention.

The described methods for rehydration and reconstitution of liposomes can alternatively be used in combination. For instance, freeze-dried liposomes may be applied to the skin from a dry pad 10 using an hand held applicator such as the steam device 20. After a period of time, allowing for some rehydration by skin moisture, either natural or added, steam or vapor may be applied using the same applicator or other independent means.

An extension of the present invention is the introduction of freeze-dried liposomes to cosmetics. In these alternative embodiments, the moisturizing, agents are encapsulated in freezedried liposomes and the liposomes mixed in a cosmetic carrier such as a lipstick cream or a facial powder. The carrier must be without significant water content to prevent premature rehydration. The objective is to allow the liposomes to be reconstituted in a the release fashion as ambient moisture and vapor is absorbed from the skin and surrounding air. As a consequence, the encapsulated moisturizer is provided to the skin in an ongoing manner. Similarly, other agents whose benefits will be enhanced by gradual application can be provided by this means. These include deodorants and fragrances.

The preceding description and examples are intended to illustrate the present invention. They are not intended to be an exhaustive presentation of all possible alternatives and persons skilled in this field will recognize that modifications or substitutions could be made to the descriptions given above that would remain within the scope of the invention.

We claim:

1. A method of skin treatment using freeze-dried liposomes comprising the steps of:

encapsulating at least one effective agent into a liposome;

freeze-drying said liposome;

depositing said encapsulated agent onto a fabric-like pad;

applying said fabric-like pad to a selected skin surface, thereby depositing said liposomes onto the skin surface.

2. A method of skin treatment according to claim 1, further comprising the step of;

rehydrating said liposomes prior to applying said pad to the selected skin surface.

3. A method of skin treatment according to claim 1, further comprising the step of:

selecting a compound capable of forming liposomes which will preferentially deliver agents to the epidermis.

4. A method of skin treatment according to claim 1, further comprising the step of;

securing said fabric-like pad to a hand-held applicator.

5. A method of skin treatment according to claim 1, further comprising the steps of;

generating steam within said applicator, and directing steam through said fabric-like pad, such that said freeze-dried liposomes are rehydrated by steam and water vapor.

6. The method of skin treatment according to claim 1, wherein;

the agent is an alpha-hydoxyacid.

7. The method of skin treatment according to claim 1, wherein;

the agent is at least one antimicrobial compound.

8. The method of skin treatment according to claim 1, wherein;

the agent is at least one proteinase.

9. The method of skin treatment according to claim 1, wherein;

the agent is at least one botanical extract.

10. The method of skin treatment according to claim 1, wherein;

the agent is at least one moisturizer.

11. The method of skin treatment according to claim 1, wherein;

the agent is at least one antioxidant.

12. A method of providing a time release cosmetic comprising the steps of:

encapsulating a skin care agent in a liposome;

freeze-drying said liposome;

mixing said liposome with at least one cosmetic carrier to form a mixture; and applying said mixture to the skin such that said liposome is deposited on the skin such as to allow rehydration over a period of time.

* * * * *